United States Patent [19]

Shanbrom

[11] Patent Number: 5,919,907
[45] Date of Patent: Jul. 6, 1999

[54] PREPARATION AND UTILIZATION OF A NOVEL STERILE ALBUMIN

[75] Inventor: Edward Shanbrom, Santa Ana, Calif.

[73] Assignee: Shanbrom Technologies LLC, Ojai, Calif.

[21] Appl. No.: 08/995,496

[22] Filed: Dec. 22, 1997

[51] Int. Cl.$^6$ .............................. C07K 1/00; A01N 43/04; A61K 33/18
[52] U.S. Cl. .................. 530/362; 530/363; 530/364; 530/416; 530/417; 530/419; 530/421; 530/427; 530/812; 530/813; 530/815; 424/78.25; 424/405; 424/406; 514/2; 514/5; 514/21; 514/59; 514/60
[58] Field of Search ..................................... 530/362, 363, 530/364, 416, 417, 419, 421, 427, 812, 813, 815; 424/78.25, 405, 406; 514/2, 5, 21, 59, 60

[56] References Cited

U.S. PATENT DOCUMENTS

| | | | |
|---|---|---|---|
| 5,071,648 | 12/1991 | Rosenblatt | 424/78.06 |
| 5,250,663 | 10/1993 | Tenold | 530/364 |
| 5,346,992 | 9/1994 | Grandgeorge et al. | 530/364 |
| 5,370,869 | 12/1994 | Shanbrom | 424/78.22 |

FOREIGN PATENT DOCUMENTS

| | | |
|---|---|---|
| WO 93/04678 | 3/1993 | WIPO . |
| WO 93/17693 | 9/1993 | WIPO . |
| WO 94/00011 | 1/1994 | WIPO . |

OTHER PUBLICATIONS

Highsmith et al., *Blood*, vol. 86, No. 2, pp. 791–796, 1995.

*Primary Examiner*—Cecilia Tsang
*Assistant Examiner*—Abdel A. Mohamed
*Attorney, Agent, or Firm*—Stefan J. Kirchanski, Esq; Graham & James LLP

[57] ABSTRACT

A method of preparing a novel, sterile, receptor rich-albumin molecule which utilizes the disinfecting properties of iodine by reacting an iodine donating material or solution with a pure preparation of albumin, and preferably subsequently removing the iodine. The resulting iodine has improved binding properties because the production method strips bacterial endotoxin and other previously bound substances from the albumin. The improved binding site capacity of the albumin product is advantageously used as an adjunct in removing toxins by means of exchange transfusions. Because iodine disinfects the albumin typical pasteurization and related additives are unnecessary.

13 Claims, No Drawings

PREPARATION AND UTILIZATION OF A NOVEL STERILE ALBUMIN

BACKGROUND OF THE INVENTION

1. Field of the Invention

In general, the invention relates to the utilization in the field of human and veterinary medicine of a novel, sterile, essentially pure preparation of albumin. More specifically, the invention involves the utilization of albumin which has been disinfected by means of pretreatment with iodine to form a sterile albumin-iodine complex; the complex subsequently being subjected to an iodine recapture process thereby yielding a pure, sterile albumin product with enhanced binding properties.

2. Description of Related Art

Normal Human Serum Albumin is a sterile solution of serum albumin often prepared from pooled blood, plasma, serum or placentas obtained form healthy human donors. Each unit of plasma used in the preparation of albumin human must be nonreactive for hepatitis B surface antigen (HB-sAg), and the product is generally pasteurized at 60° C. for 10 hours. Such albumin solutions contain no clinically important isoagglutinins or other antibodies and may be administered without regard to the recipient's blood group or Rh factor; none of the recognized components of the clotting mechanism of normal blood or plasma is present in albumin human solutions. *AHFS Drug Information*, 914, (1995)

Serum albumin is an important factor in the regulation of plasma volume and tissue fluid balance through its contribution to the colloid oncotic pressure of plasma. Albumin normally constitutes 50–60% of plasma proteins and, because of its relatively low molecular weight (66,300–69,999), exerts 80–85% of the colloidal oncotic pressure of the blood. Ibid.

The major clinical use of albumin is as a plasma volume expander and there are 50 years of experimental evidence to document its effectiveness. It is most widely used for its oncotic properties in the resuscitation of patients with an acutely diminished intravascular volume. It has beneficial effects on viscosity and is used for pump-priming in cardiopulmonary bypass surgery and hemodialysis. Although correction of an underlying disease process is necessary to correct defects in albumin production, exogenous albumin has been administered as an acute means of correcting hypoproteinemic states.

Albumin's properties as a transport protein have been used advantageously in binding bilirubin during therapy of hemolytic disease of the newborn. *The Pharmacologic Approach to the Critically Ill Patient*, 227 (1988) Albumin binds and functions as a carrier of intermediate metabolites (including bilirubin), trace metals, some drugs, dyes, fatty acids, hormones, and enzymes, thus affecting the transport, inactivation, and/or exchange of tissue products. *AHFS Drug Information*, 914 (1995) The importance of the inherent ability of albumin to bind various endogenous and exogenous substances accelerates as a foci for research dollars in a growing market.

Although albumin can bind a wide variety of substances in proportion to their lipophilicity, the protein has a particularly high affinity for weakly acidic substances, which at physiologic pH are present predominantly in the anionic form. Electrostatic forces are, therefore, likely to be important in binding, with additional contributions from hydrogen bonding and hydrophobic interactions. Binding is usually reversible, with association and dissociation time-constants typically being in the millisecond range. Mass action kinetics apply, predicting saturability at high ligand concentrations and competition among structurally related substances for common sites of interaction. *Principles of Pharmacology, Basic Concepts & Clinical Applications*, 49 (1995) There are three distinct classes of binding sites on the albumin molecule. Competitive displacement studies have been performed with warfarin, diazepam, and digitoxin as specific markers of each of these binding domains. Information so obtained has provided a useful framework within which to understand and predict drug-drug interactions attributable to alterations in binding to plasma albumin. Ibid A well known example of the applicability of albumin binding sites to the detoxification of a neurological toxin involves the development of neonatal kernicterus after the administration of certain antibacterial sulfonamides. Early in the neonatal period, the breakdown of fetal hemoglobin releases large amounts of bilirubin that cannot be efficiently metabolized by conjugation to a more water-soluble metabolite due to the immature state of the hepatic enzyme, glucuronyl transferase in newborns. Bilirubin is extensively bound to albumin and this interaction (involving "warfarin-type" binding sites) is critical in preventing excessive increases in plasma concentrations of free bilirubin that, given the incomplete formation of the neonatal blood-brain barrier, can result in severe neurologic damage.

With regard to the present invention, it follows logically then, that if we can increase the number of available binding sites by administering a sterile, pure albumin which by nature of its production method, has a relative increase in the number of available binding sites in proportion to the number sites available on untreated albumin, we can effectively increase the margin of safety for patients against the possibility of bilirubin induced brain damage which results from displacement of toxic products from saturated binding sites on untreated albumin proteins.

The literature supports just such a proposition by reporting that, "In the treatment of hyperbilirubinema and erythroblastosis fetalis, albumin human is used as an adjunct in exchange transfusions; its bilirubin-binding activity reportedly reduces the number of transfusion required by increasing the amount of bilirubin removed with each transfuision *ASHS Drug Information* 914 (1995) This suggested use for the present invention of a purified albumin is intended to be representative only and is not meant to limit future or other uses of the product. Indeed, the use of albumin human as a transport protein to bind other toxic agents remains investigational and in light of the import of albumin binding and known albumin-drug and drug-drug interactions, the range of applications seems broad.

It is particularly in light of a demonstrable saturability of albumin binding sites that the import of one of the unique properties of my invention is revealed. Because albumin has the ability to bind any number of variable endogenous and exogenous entities, some of the aforementioned binding sites on untreated albumin can become saturated with superfluous agents added during the usual fractionation of plasma to produce albumin resulting in a concomitant decrease in the relative number of available binding sites on the protein molecule. A more efficacious application for this scarce resource can be realized with the prudent utilization of a sterile, purified albumin in which effectively all of the potential binding sites are available for use, thereby facilitating the ability of albumin to act as a carrier agent, either for the delivery of some product or for the removal of some toxic product according to the needs of the time.

The albumin product embodying this invention must be pure and sterile in order to maximize the number of available binding sites on the protein molecule itself. Prior inventors have taken numerous directions in pursuing various products with analogous desirable characteristics.

U.S. Pat. No. 5,346,992 describes a process for isolating albumin from supernatant IV, and in particular IV-4, or from COHN's fraction V or from plasma supernatant or fraction of analogous composition derived from an alcoholic or non-alcoholic anion exchange column with binding of albumin to the column, and then elution, and one step on a hydrophilic anion exchange column. Albumin thus obtained having a purity >99% by cellulose acetate electrophoresis, being free from impurities detected by crossed immunoelectrophoresis and from polymers. Other similar ventures are described in that publication which have yielded purities of >96%, 96.9%–98.9%, and > or =99% and are incorporated herein by reference.

Previous albumin preparations suffered the problem of containing high amounts of aluminum as a contaminant along with it's associated toxicities, particularly in patients with impaired renal function who may be predisposed to suffering the detrimental effects of aluminum accumulation. U.S. Pat. No. 5,250,663 discloses a composition which comprises a solution of human serum albumin essentially free of chemicals used in processing. The preparation is also essentially free of metals such as aluminum. The composition is 100% pure by cellulose acetate electrophoresis and is essentially monomeric when tested by high pressure liquid chromatography. The preparation had a substantially longer shelf life and activity factor than other currently available products at that time. Novel applications of process methodology are taught in the preparation of this composition and a novel preparation result from essentially non hemoglobin containing albumin sources such as Source Plasma (Human) are discussed. Techniques and references are taught therein and are incorporated here by reference.

Once albumin has been separated from other various blood constituents, including other proteins, depending upon the nature of the origin of the albumin, there frequently remains other contaminants which need to be removed before the albumin is pure enough to meets the needs of the present invention. U.S. Pat. No. 5,250,662 provides a process for separating albumin from an impure protein fraction containing albumin. Contaminants, in an aqueous solution of the impure protein fraction containing albumin, are precipitated from the solution at a pH of from about 4.5 to about 4.7. Additional contaminants that remain soluble are bound to an anion-exchange resin. After the precipitated and anion-exchange-bound contaminants are removed from the albumin-containing solution, the pH of the solution is adjusted to from about 4.7 to about 6.1, and additional contaminants are precipitated. Further contaminants are then bound to an anion-exchange resin, and these precipitated and anion-exchange-bound contaminants are removed from the albumin-containing solution.

U.S. Pat. No. 4,197,238 discusses a method for purifying albumin, especially from human placenta, by removing blood group substance and hypotensive substances with polyethylene glycol to precipitate contaminant proteins containing blood group antigens and recovering albumin from the supernatant fluid. This patent discusses various methods of purifying albumin for infusion including many of the various shortcomings of these methods. The references from this patent are incorporated herein by reference.

An early patent, U.S. Pat. No. 4,169,829 includes a stepwise explanation of purification of albumin from frozen placenta, placental blood or other hemolyzed blood, by removing in a stepwise fashion, hemoglobin, enzymes and blood group substances. The value of this process is that when practiced according to the present invention, the albumin is well received by the receiving organism and does not cause antigenic and other reactions which may occur with prior art albumin preparations prepared from such raw materials.

The above methods of preparing albumin tend to yield product with problems or shortcomings in at least three areas. First, in all cases the albumin must still be "pasteurized" to insure a non-infectious product. Pasteurization is the process of subjecting the albumin obtained by whatever means to a heat treatment process wherein the product is sterilized by filtration and distribution aseptically into containers which are sealed to exclude micro-organisms and maintained at 59.5 to 60.5° C. for 10 hours. Not only does this process kill many pathogens, but it also results in precipitation of a portion of the contaminating proteins which adversely affects the clarity of the final albumin solutions. However, to protect the albumin itself from precipitation additional substances such as caprylic acid are usually added. These additives bind to the albumin and stabilize it. Unfortunately, the final product then has at least some of its binding sites filled by the caprylate.

A second problem is that many of the above purification processes result in a lower overall yield of albumin due to the additional ethanol precipitation or the heating steps employed to ensure high purity. Furthermore, heating of the albumin results in an increase in the albumin polymer content however, high monomer contents are the desirable state of the art albumin product, since it has been suggested that albumin polymers are cleared more rapidly from the circulation than are albumin monomers, effectively resulting in the reduction of the concentration of infused albumin. It has also been suggested that the polymer form of albumin may produce an undesirable immunological response. See, U.S. Pat. No. 5,250,662.

Finally, overall albumin binding capacity is often compromised by the presence of endotoxin, a lipoidal material produced by bacteria. One of the natural functions of albumin is probably to bind such materials, but where do they come from during albumin fractionation under controlled laboratory conditions? The number of bacteria present in circulating plasma should be zero; however, when plasma is donated it becomes bacterially contaminated because it is impossible to maintain total sterility. If albumin is reclaimed from placenta or cord blood, the possibility of bacterial contamination is even higher. Although the blood or plasma is generally refrigerated during processing, considerable bacterial growth still occurs. Although these bacteria are ultimately killed by pasteurization or other steps, they still release considerable endotoxin which then binds to the albumin.

The current inventor has explored the use of iodine complexes in the treatment of blood and blood complexes in considerable detail. For example, the inventor's U.S. Pat. No. 5,370,869 discloses a method of disinfecting platelet-bearing liquid by contacting the liquid to be cleansed with solid povidone-iodine to expose the platelet-bearing liquid to iodine and thus kill pathogenic organisms therein, and thereafter removing the liquid from contact with the solid povidone-iodine.

Additional aspects of the inventor's work are reported by Highsmith et al., *Blood*, 86(2): 791–96 (1995). This study explored the use of liquid iodine for inactivation of several lipid and nonlipid enveloped viruses in an antithrombin III (AT-III) concentrate. Iodine at levels of about 0.01% to about 0.02% caused between 43% and 94% loss of AT-III activity, as well as degradation of AT-III as shown by sodium dodecyl sulfate-polyacrylamide gel electrophoresis and Western blot analysis.

If the use of albumin in the medical and veterinary arts is truly to be maximized, simply producing a pure albumin does not address all of the concerns of those who would employ it. That is, not only is it desirable for the albumin to be pure, but it must also be sterile. We live in a world of increasing risk with regard to transmitted diseases and their growing resistance to antimicrobial therapy. Gone are the days when the administration of a single injection of a drug such as penicillin could cure even the most woeful diseases. Today, we are faced with challenges and risks that carry the gravest consequences. Unfortunately, even as of this writing, infection with the AIDS virus leaves only the slimmest hope for normal longevity. The author in U.S. Pat. No. 5,204,324 has addressed a technique for inactivating at least one of the more prevalent pathogenic viruses found in animal fluids and tissues.

Clearly, a method of producing not only a pure, but also a sterile albumin which would allow maximal use of available binding sites would represent a valuable asset in various albumin-type therapeutic interventions.

OBJECT AND SUMMARY OF THE INVENTION

It is the object of the present invention to provide a process of producing a sterile albumin protein by applying the exceptional disinfection properties of iodine to a purified albumin molecule; and It is a further object of the invention to produce a pure, sterile albumin molecule with effectively a substantially increased number of available binding sites thereon, by subsequently removing the iodine from the albumin after sterilization has been completed.

The current inventor discovered that, in spite of the known fact that albumin generally destroys the biocidal power of iodine, albumin, when reacted with sufficient iodine, forms a complex somewhat analogous to the previously-known iodophors such as povidone-iodine while maintaining significant advantages over povidone-iodine. The material is generally nontoxic, non-immunogenic and disinfects with a minimal damage to cell and tissues. Although much of the iodine complexed with albumin becomes covalently bound, given sufficient time, a significant portion of the iodine is available for contact and reaction with various organisms to effectuate significant "killing power." Thus, iodine treatment of albumin results in iodine saturated protein in which any pathogens present are readily and rapidly destroyed. That is, the goals of a sterile albumin can be met without pasteurization and its required additives.

The invention thus encompasses a process of preparing sterile albumin comprising reacting substantially pure albumin, preferably unsterilized, unstabilized, and delipidated, with sufficient iodine-containing reagent to substantially saturate all binding sites thereon. In general, the resulting albumin-iodine complex will have the same sterilizing effect on bacteria, virus, or other pathogenic organisms as would occur in processes in which povidone-iodine is used. The result is a sterile albumin product. Thereafter, the iodine is removed by bringing the albumin-iodine containing solution into contact with an iodine absorbing agent.

The invention is further embodied in a sterile albumin molecule with a substantially increased number of binding sites created by the process of forming the albumin-iodine complex, the complex to provide activity equivalent to a concentration of about 0.01 weight percent to about 1 weight percent iodine (resulting from the addition of oxidizing iodine to albumin in the formation of albumin-iodine complex), allowing sterilization of the albumin to occur, and subsequent removal of the iodine by bringing the complex in contact with an iodine absorbing agent. The removal of iodine from its respective albumin binding sites results in an increase in the absolute number of available binding sites on the albumin molecule. This result is not as paradoxical as it may at first appear. The increase in binding sites appears to come from an uncovering of binding sites by the removal of endotoxin. Of course, the absolute number of sites is also greater because caprylate and other stabilizing additives are avoided.

The invention is further embodied in a method of using a sterile albumin with an increased number of available binding sites as a therapeutic means of removing toxic substances by adding the "site-rich" albumin to a solution as an adjunct to exchange transfusions for the treatment of hyperbilirubinemia in hemolytic disease of the newborn. See, REMOVAL OF INDIRECT ACTING BILIRUBIN BY ALBUMIN BINDING DURING INTERMITTENT PERITONEAL DIALYSIS IN THE NEWBORN. *Acta Paediatr Scand* 1969; 58:171–172

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for the preparation and use of a sterile albumin with substantially increased binding site capacity.

The sterilized albumin of the present invention is prepared beginning with substantially pure albumin. The albumin may have traces of other proteins and biological materials, of course, and term "pure" is used in the sense common in reference to biological isolates that inherently contain some biologicals in addition to the principal constituent. The degree of purity required is dependent upon the intended use of the final product, and the presence of trace amounts of other materials is not per se detrimental to the present invention. It is recognized however, that the more pure the starting preparation, the less chance that superfluous materials will utilize desirable binding sites on the albumin molecule and diminish the potential efficacy of the final product.

Nondenatured, nonpasteurized albumin free of stabilizers such as caprylate and fatty acids, etc., is greatly preferred. Indeed, the time consuming and expensive steps of killing microbes which are required in the normal preparation of albumin is essentially surplus or irrelevant, since all microbes will be killed by the iodine. Iodine in any form may be reacted with the albumin using any convenient technique or apparatus. It is possible to form albumin-iodine complex by adding iodine to an albumin solution; for example, the albumin solution can be contacted with an iodine source such as iodinated ion exchange resin. This method usually creates an atmosphere where there is an excess of free iodine in the solution.

Therefore, it has been found convenient to use an insoluble iodine donating material such as cross-linked povidone-iodine or iodine-ion exchange resin as the iodine source because these materials provides a convenient source of iodine, have high iodine content, and do not add other chemicals or constituents to the resulting albumin-iodine. Alternatively, other insoluble iodine binding agents such as starch, polyvinyl acetate copolymer (vinyl-acetate-alcohol-acetate copolymer, a reaction product of formaldehyde and polyvinyl alcohol) or even cross-linked albumin or other protein may be used as an iodine source. The general goal is to rapidly saturate albumin with iodine without adding a significant amount of free soluble iodine. Preferably, a solution of albumin is passed through a bed or column of a solid, insoluble iodine source where it becomes approximately saturated with iodine.

Generally, albumin will covalently bind at least about 0.01 weight percent iodine. Much of the iodine in excess of this amount will be available for disinfectant purposes. Generally, a concentration of iodine at 1 weight percent is more than enough to kill or inactivate any known microbes that may be present in the albumin. The iodine is allowed to remain in contact with the albumin for a period of time to kill the microbes. It may be somewhat difficult to predict the minimum contact time to cause adequate disinfection. The duration of disinfection is a function of the free iodine concentration and the minimum inhibitory concentration (MIC) of the possible contaminating organisms. Generally, the disinfection is instantaneous being complete by the time the albumin is removed from the iodine donating source. It may be advantageous to wait a period of time (e.g. one to several hours) to ensure disinfection. Then the iodine is stripped from the albumin to give the final product.

In one embodiment, an aqueous solution containing human serum albumin is passed through an iodination cartridge. The iodination cartridge comprises an insoluble source of oxidizing iodine such as discussed above. If suitable materials and reliable solid particle barriers are used, a very small amount of crystalline iodine could be used. However, this approach presents manufacturing and storage difficulties that need not be faced if an insoluble iodine donor is used as the source of iodine. By using an insoluble iodine-binding material to deliver iodine to the albumin very little, if any, free iodine is ever present. The albumin solution is allowed to flow through the iodination cartridge and into a collecting vessel for storage if additional disinfection time is desired. In the iodination cartridge, the albumin solution adsorbs and/or absorbs iodine to form albumin-iodine complex. The oxidizing iodine content of the albumin-iodine complex coupled with any available free iodine, effectively kills or inactivates viruses, bacteria, and other microorganisms in the albumin solution.

The albumin is then stripped of iodine by passing it through a column of a material that strongly binds iodine. Although a number of different iodine binding material such as cross-linked PVP and starch are possible iodine-binding agents, the currently preferred materials consist of anion exchange resins such as Q-sepharose or DEAE Sephadex (derivatized carbohydrate polymers manufactured by Amersham-Pharmacia) or Purolite (derivatized polystyrene resin manufactured by Purolite Corporation) or a porous sponge made from polyvinyl acetal (PVA) (a polymer of vinyl alcohol, vinyl acetate and formaldehyde, also known as polyvinyl acetal-acetate copolymer). It has been found that passing an iodinated albumin solution through a sufficient amount of one of these capturing agents results in essentially total removal of iodine. The amount of iodine present can be measured by adding a reducing agent (e.g., ascorbate or sulfite) following which the iodide concentration is measured with an iodine sensitive electrode as is well-known to those of ordinary skill in the art. If significant amounts of iodide are detected, then the amount of capture material is increased in subsequent runs. If the iodine removal is effected within 2–3 hours of the iodination process, there will be essentially no covalently bound iodine left on the albumin. If removal happens after a longer period of time, there will be an increasing amount of covalently bound iodine in the albumin.

An important discovery is that albumin can be iodine sterilized with all of the iodine subsequently removed to yield a fully functional albumin molecule. What was even more exciting and unexpected was the discovery that the resulting albumin is actually superior in binding capacity to the normally available product. Part of this improvement is due to the avoidance of pasteurization and its concomitant additives. However, a significant improvement appears to result from the removal of residual endotoxin from the albumin. If albumin is mixed into a medium in which bacteria have grown and then been heat-killed, the albumin will absorb a large amount of endotoxin. The presence of endotoxin can be demonstrated with any of a number of tests such as the well-known limulus test. However, if this endotoxin-saturated albumin is subjected to the present invention, subsequent tests show a total removal of endotoxin. A possible explanation for this surprising result is that the lipoidal endotoxin absorbs considerable iodine, possibly even enough to alter its binding ability to the albumin. When the albumin passes through the iodine-capture material, the iodine saturated endotoxin preferentially binds to the capture material and, like the iodine, is stripped from the albumin.

A number of different substances that are readily detectable can be added to albumin as a way of monitoring the binding capacity of the albumin. In the following experiments iodine treatment was effected by passing the albumin solution through a one centimeter thickness of iodine-treated PVA sponge (available from the Merocel Corporation of Mystic, CT). The PVA material used contained approximately 16% by weight iodine. The excess iodine was removed by passing the solution through a five-times greater thickness of plain PVA sponge. In each case the sponges were compressed to remove clinging albumin solution. The removal of iodine from the albumin solution can be monitored by a darkening of the PVA. If the PVA darkens all the way through the layer, then there is a likelihood that free iodine is passing through; this is an indication that the thickness of the plain PVA should be increased. For these experiments ordinary purified (pasteurized) albumin was used.

In a first experiment 50 ml aliquots of 10% human serum albumin (HSA) were treated as just explained using a 60 cc syringe to hold the pads with the syringe plunger serving to force the liquid through the PVA and squeeze the PVA at the end of the run. Triton X-100 (1.0 ml of a 5% aqueous solution) was added to 20 ml aliquots of either the treated or untreated HSA. A Triton-containing solution foams heavily when shaken. However, if relatively small amounts of Triton are added to HSA, the resulting mixture foams much less than the same quantity of Triton added to a volume of water. This suggests that when Triton is bound by albumin, its ability to foam is reduced or eliminated. When 1.0 ml of 5% Triton was added to 20 ml of 10% HSA, the untreated HSA foamed very heavily when shaken. However, the iodine treated HSA produced only moderate foam. This suggests that the iodine treatment increased the ability of HSA to bind Triton. An additional version of this experiment explored the binding ability of the iodine treated albumin without rigorously removing the iodine first. Surprisingly, the mere presence of iodine appeared to noticeably enhance the binding of Triton. It seems likely that the iodine displaces interfering substances from the albumin and that the Triton is then capable of displacing the iodine. In other words, tightly bound materials are displaced by iodine (perhaps in a mass action fashion). Subsequently, other materials such as Triton can readily displace the iodine resulting in enhanced binding.

In a second experiment iodine treated or untreated 10% HSA were compared in terms of their ability to bind either methylene blue dye, canola oil or hemoglobin. In the case of methylene blue the dye solution was added dropwise to equivalent volumes of either treated or untreated HSA. It took about twice as much methylene blue to produce an equivalent color with the treated albumin. Presumably the bound dye is less efficient at absorbing light than is the free dye. In the case of canola oil the oil was added dropwise and the mixture was shaken to facilitate oil binding. Oil was added until a layer of oil remained following the mixing (i.e., the HSA became saturated with oil). Again, the treated HSA was able to absorb slightly more than twice the volume of oil as the untreated albumin. Finally, to maintain equivalent colors about three times as much hemoglobin solution must be added to the treated as to the untreated HSA. These results show that iodine treatment greatly increases albumin's ability to bind a wide range of substance. Like in the first experiment enhanced binding could also be shown after iodine treatment even if the free iodine was not all removed by an iodine capture step.

The inventor's hypothesis is that the iodine treatment strips interfering materials (probably including endotoxin) from the albumin. Unfortunately, additives required for pasteurization (discussed above) undoubtedly fill a significant number of binding sites. This can be demonstrated by adding iodine solution (Lugol's solution, 5% iodine and 10% potassium iodide) to aliquots of either commercial pasteurized albumin or "raw" albumin that had not seen either additives or pasteurization. In this case a 10 ml aliquot of pasteurized 10% HSA could accept 200 μl of iodine solution before it became brown in color. The "raw" HSA could accept about five times as much iodine solution before taking on an equivalent brown color. Similarly, if the albumin solutions were passed through equivalent volumes of solid iodine donating material (40% iodine DEAE cross-linked dextran [Sephadex® from Amersham-Pharmacia Biotech] in this case), the pasteurized HSA became dark brown and nearly opaque while the "raw" HSA remained transparent and only light amber in color.

As expected, repeating the various binding tests showed that "raw" albumin was able to bind several times as much of each substance as pasteurized albumin (four times as much methylene blue and six times as much hemoglobin). In this case the iodine treatment resulted in only a moderate improvement in binding capacity. This suggests that much of the loss of capacity is due to the various stabilizing additives used during pasteurization. Of course, the heat treatment may also damage the albumin. The moderate improvement following iodine treatment of "raw" albumin may represent removal of endotoxin or some other material naturally bound to the albumin. The point that should be kept in mind is that the iodine treatment kills pathogens obviating the need for pasteurization and binding reducing additives.

The discovery that iodine treatment enhances the binding capacity of albumin can be utilized in at least two different ways. Albumin can be treated with iodine and them immediately used in any procedure based on the ability of albumin to bind toxins, etc. However, it should be appreciated that there may be considerable reluctance to use an iodine-containing preparation in patients. If at least about 24 hrs elapses between iodine treatment and use of the albumin most or all of the iodine will have become covalently bound to the albumin or converted into iodide ion. That is, little if any free active iodine will remain. However, there may still be a reluctance to treat a patient with even covalently bound iodine. The second way of practicing the invention is to remove free iodine with an absorbing material such as PVA. If anion exchange resins are employed, iodide can also be removed from the enhanced albumin.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method of preparing an improved sterile albumin molecule comprising the steps of:

adding iodine to an albumin solution;

allowing the albumin solution and iodine to incubate together for sufficient time to ensure destruction of any microorganisms and to displace previously bound substances; and contacting the albumin and iodine solution with an iodine-capture agent to remove iodine from the albumin, thereby producing improved albumin.

2. The method of claim 1, wherein iodine in the form of an aqueous iodine solution is added to the albumin solution.

3. The method of claim 1, wherein iodine in the form of an insoluble iodine donating material comprising a matrix material to which iodine is added to the albumin solution, the matrix material being selected from the group consisting of insoluble polyvinylpyrrolidone, insoluble starch, insoluble protein, insoluble dextran polymer, ion exchange resin and polyvinyl acetal.

4. The method of claim 1, wherein the iodine capture agent is selected from the group consisting of insoluble polyvinylpyrrolidone, ion exchange resin and polyvinyl acetal.

5. A sterile receptor-site rich albumin prepared by a process comprising the steps of adding iodine to an albumin solution, incubating a resulting mixture for a sufficient time to kill any pathogens in the mixture and to displace previously bound substances, and contacting the resulting mixture with an iodine capturing material to remove iodine.

6. The sterile receptor-site rich albumin of claim 5, wherein iodine is added as an aqueous iodine solution.

7. The sterile receptor-site rich albumin of claim 5, wherein iodine is added as an insoluble iodinating material comprises a matrix material to which iodine has been bound, the matrix material being selected from the group consisting of insoluble polyvinylpyrrolidone, insoluble starch, insoluble protein, insoluble dextran polymer, ion exchange resin and polyvinyl acetal.

8. The sterile receptor-site rich albumin claim 5, wherein the iodine capture material is selected from the group consisting of insoluble polyvinylpyrrolidone, ion exchange resin and polyvinyl acetal.

9. A method of using the sterile receptor-site rich albumin of claim 5, whereby the sterile receptor-rich albumin is added to a dialysate solution as an adjunct to exchange transfusions for the treatment of hyperbilirubinemia in hemolytic disease of the newborn.

10. A method of removing endotoxin from albumin comprising the steps of:

adding iodine to an albumin solution;

incubating a resulting iodine albumin solution for a predetermined time less than one hour to ensure interaction between endotoxin and iodine; and contacting the solution with an iodine-capture agent to remove iodine and endotoxin from the albumin.

11. A method of preparing an improved sterile albumin molecule comprising the steps of:

adding iodine to an albumin solution; and allowing the albumin solution and iodine to incubate together for sufficient time to ensure destruction of any microorganisms and to displace previously bound substances.

12. The method of claim 11, wherein iodine in the form of an aqueous iodine solution is added to the albumin solution.

13. The method of claim 11, wherein iodine in the form of an insoluble iodine donating material comprising a matrix material to which iodine is added to the albumin solution, the matrix material being selected from the group consisting of insoluble polyvinylpyrrolidone, insoluble starch, insoluble protein, insoluble dextran polymer, ion exchange resin and polyvinyl acetal.

* * * * *